United States Patent [19]

Taicher et al.

[11] Patent Number: 5,698,979
[45] Date of Patent: Dec. 16, 1997

[54] METHOD FOR NMR DIFFUSION MEASUREMENT

[75] Inventors: Gersh (Zvi) Taicher; Arcady Reiderman, both of Rehovot, Israel

[73] Assignee: Western Atlas International, Inc., Houston, Tex.

[21] Appl. No.: 641,960

[22] Filed: May 1, 1996

Related U.S. Application Data

[63] Continuation-in-part of Ser. No. 606,089, Feb. 23, 1996.

[51] Int. Cl.[6] .............................. G01U 3/32; G01U 3/18
[52] U.S. Cl. ............................................ 324/303; 324/300
[58] Field of Search ................................ 324/300, 303, 324/307, 309; 128/653.2, 543.3

[56] References Cited

U.S. PATENT DOCUMENTS

| | | | |
|---|---|---|---|
| 4,717,877 | 1/1988 | Taicher et al. | 324/303 |
| 5,212,447 | 5/1993 | Paltiel | 324/303 X |
| 5,428,291 | 6/1995 | Thomann et al. | 324/303 |

OTHER PUBLICATIONS

J. Glasel et al, "On the Interpretation of Water Nuclear Magnetic Resonance Relaxtion Times in Heterogeneous Media," Journal of the American Chemical Society, vol. 96, No. 4 Feb. 20, 1974, pp. 970–977.

L. Latour et al, "Time–Dependent Diffusion Coefficient of Fluids in Povrous Media as a Probe of Surface–to–Volume Ratio," Journal of Magnetic Resonance, Series, A, vol. 101, pp. 342–346 (1993) Academic Press, Inc.

Primary Examiner—Sandra L. O'Shea
Assistant Examiner—Roger C. Phillips
Attorney, Agent, or Firm—Richard A. Fagin

[57] ABSTRACT

A method of measuring motion properties of nuclei within pore spaces of a porous medium. The method includes applying a static magnetic field to the medium to polarize the nuclei, generating a first magnitude of magnetic field gradient within the pore spaces of the medium, applying a radio frequency magnetic field to excite the nuclei, receiving nuclear magnetic resonance signals from the nuclei, and calculating the motion properties from rates of decay of the amplitude of the nuclear magnetic resonance signals. A preferred embodiment includes applying a static magnetic field having a first amplitude, a second amplitude and an amplitude gradient, applying the radio frequency magnetic field at a first frequency to excite the nuclei within the first static magnetic field amplitude, receiving resonance signals at the first frequency, applying a radio frequency magnetic field at a second frequency to excite the nuclei within the second static magnetic field amplitude, receiving resonance signals at the second frequency, and calculating the motion properties from the difference in rates of decay of the amplitudes of the resonance signals from the first and the second frequencies.

16 Claims, 3 Drawing Sheets

METHOD FOR NMR DIFFUSION MEASUREMENT

CROSS REFERENCE TO RELATED APPLICATIONS

This application is a continuation in part of patent application Ser. No. 08/606,089, filed on Feb. 23, 1996, and entitled "Nuclear Magnetic Resonance Sensing Method and Apparatus".

BACKGROUND OF THE INVENTION

1. Field of the Invention

The invention is related to the field of nuclear magnetic resonance (NMR) measurement methods. More specifically, the invention is related to methods for determining the diffusion properties of fluids within porous media.

2. Description of the Related Art

The use of nuclear magnetic resonance (NMR) measurements to determine diffusion properties of fluids within porous media is described, for example, in L. L. Latour et al, *Time-Dependent Diffusion Coefficient of Fluids on Porous Media as a Probe of Surface-to-Volume Ratio*, Journal of Magnetic Resonance, vol. 101, pp 342–346 (1993). A technique described in the Latour reference is referred to as the "pulsed gradient stimulated spin echo" technique, which can generally be described as performing NMR spin-echo measurements by selectively superimposing a gradient magnetic field upon a static magnetic field used to polarize nuclei in the materials being analyzed (the fluid within the porous medium). This pulsed gradient technique has the particular advantage of reducing the effects of internal magnetic field gradients which are generated as a result of differences in the magnetic susceptibility between the porous solid and the fluid disposed within the pore spaces when the polarizing static magnetic field is applied to the porous medium.

These internal magnetic field gradients, $G_i$, for a particular simplified model, can be estimated by an expression described in, J. A. Glasel and K. H. Lee, *On the Interpretation of Water Nuclear Magnetic Resonance Relaxation Times in Heterogeneous Systems*, Journal of the American Chemical Society, vol. 96, p 970 (1974):

$$G_i = \frac{H_0 \Delta \chi}{4 R_p} \quad (1)$$

where $H_0$ represents the magnitude of the applied static magnetic field, $\Delta_\chi$ represents the difference in the magnetic susceptibility between the fluid and the solid matrix (the porous medium) and $R_p$ represents the effective radius of the pores in the matrix.

A property of the porous medium determined from the laboratory experiments using the pulsed gradient technique disclosed in the Latour reference is the so-called "self-diffusion constant", which is related to the mobility of the fluid in the pore spaces of the matrix.

U.S. Pat. No. 5,212,447 issued to Paltiel describes a method and apparatus for determining the self-diffusion constant of earth formations penetrated by a wellbore. The Paltiel '447 patent discloses applying a static magnetic field and a gradient magnetic field to a region of interest in the earth formation, applying a radio-frequency (RF) magnetic field having a frequency corresponding to the magnetic field strength in the region of interest and a duration selected to cause 90 degree reorientation of the magnetic moments of nuclei of the earth formations, allowing a predetermined time interval to elapse, and applying refocusing RF magnetic field pulses to the earth formation so as to enable detection of NMR spin-echo signals. The spin-echo measurement sequence can be repeated using a different value of predetermined time interval, or a different value of gradient magnetic field. The self-diffusion constant D and transverse relaxation time (referred to as $T_2$) are determined from the spin-echo signal amplitudes. The method disclosed in the Paltiel '447 patent generally describes determination of the self-diffusion constant by measuring amplitudes of the spin-echoes. The self-diffusion constant can be derived from the spin echo amplitudes by the following expression:

$$A(n) = A \exp\left[ -2n\tau \left( \frac{1}{T_2} + \frac{D\gamma^2 G^2 \tau^2}{3} \right) \right] \quad (2)$$

where A represent the spin-echo signal amplitude at zero time, A(n) represents the amplitude of the n-th spin echo signal, γ represents the gyromagnetic ratio of the nuclei subject to the NMR excitation (which are usually hydrogen nuclei), τ represents the time interval between successive radio frequency spin-reorientation pulses and G represents the gradient of the magnetic field. In equation (2), the independent variables are the magnetic field gradient G and the time between spin-reorientation pulses τ. The amplitude of the static magnetic field and the internal magnetic field gradients are not part of equation (2).

The Paltiel '447 patent discloses several means for changing the gradient magnetic field, including changing the frequency of the RF magnetic field. Changing the RF magnetic field frequency induces the nuclear magnetic resonance condition within a different amplitude static magnetic field, and in the apparatus disclosed in the Paltiel '447 patent, a magnet forming part of the NMR logging apparatus generates a static magnetic field having a field gradient related to the static field amplitude. By changing the RF magnetic field frequency, the static magnetic field amplitude in which the resonance condition is generated is thereby changed. The structure of the magnet disclosed in the Paltiel '447 patent provides that the gradient magnetic field will be different as well, because the static field gradient of the magnet in the Paltiel patent is directly related to the amplitude of the static magnetic field. The multiple frequency method described in the Paltiel '447 patent, however, does not account for the internal magnetic field gradients (and these internal gradients are different for each frequency used) developed within porous media when there is a difference between the magnetic susceptibility of the fluid and the matrix. Failure to account for the internal gradients can result in error in the diffusion constant so determined.

Another means to perform diffusion constant measurement disclosed in the Paltiel '447 patent is application of a switched gradient magnetic field to perform the pulsed gradient measurement technique similar to the one described in the Latour reference, supra. However, the pulsed gradient technique described in the Latour reference includes a static magnetic field having substantially zero gradient, and the applied gradient is switched in opposite directions. The pulsed gradient technique described in the Latour reference has been quite successful for making measurements of the self-diffusion constant in the laboratory, but has generally been impractical to implement in a well logging instrument, particularly because of the very high electrical power requirements for inducing the switched gradient field.

Accordingly, it is an object of the present invention to provide a means for determining the self-diffusion constant of porous media from NMR spin-echo measurements which does not require the application of a static magnetic field gradient to the media.

It is another object of the present invention to provide a means for determining the self-diffusion constant of fluids within pore spaces of porous media particularly suitable for well logging due to the internal magnetic field gradients induced therein.

SUMMARY OF THE INVENTION

The present invention is a method of measuring the motion properties of nuclei within pore spaces of a porous medium. The method includes applying a static magnetic field having a first amplitude to polarize the nuclei in the pore spaces of the medium, generating a first magnitude of magnetic field gradient within the pore spaces, applying a radio frequency magnetic field at a first frequency to excite the nuclei, receiving nuclear magnetic resonance signals from the nuclei at the first frequency, and calculating the motion properties from the rates of decay of the amplitude of the nuclear magnetic resonance signals.

A preferred embodiment of the invention includes applying a static magnetic field having a first amplitude, a second amplitude and an amplitude gradient to polarize the nuclei, applying a radio frequency magnetic field at a first frequency to excite the nuclei within the first static magnetic field amplitude, receiving nuclear magnetic resonance signals from the excited nuclei at the first frequency, applying a radio frequency magnetic field at a second frequency to excite the nuclei within the second static magnetic field amplitude, receiving nuclear magnetic resonance signals at the second frequency, and calculating the motion properties from the difference in rates of decay of the amplitudes of the resonance signals from the first and the second frequencies.

DESCRIPTION OF THE PREFERRED EMBODIMENT

1. Description of the Apparatus

Figure 1:
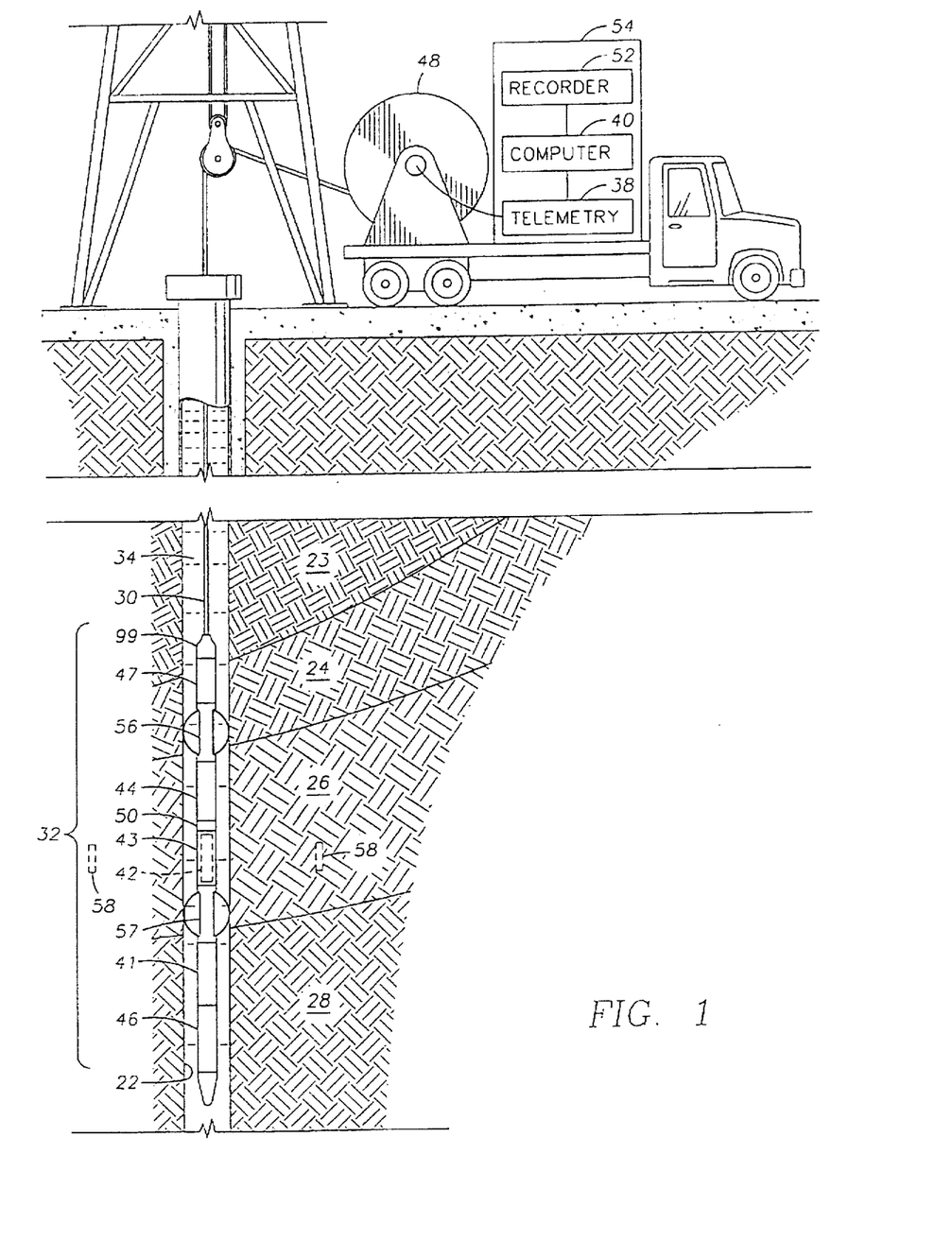
FIG. 1 shows a string of logging tools disposed within a wellbore penetrating earth formations.

FIG. 1 shows a well logging apparatus disposed in a wellbore 22 penetrating earth formations 23, 24, 26, 28 for making measurements of properties of the earth formations 23, 24, 26, 28. The wellbore 22 in FIG. 1 is typically filled with a fluid 34 known in the art as "drilling mud". A "sensitive volume", shown generally at 58 and having generally cylindrical shape, can be disposed in one of the earth formations, shown at 26. The sensitive volume 58 is a predetermined portion of the earth formations 26 in which nuclear magnetic resonance (NMR) measurements are made, as will be further explained.

A string of logging tools 32, which can include an NMR apparatus according to the present invention, is typically lowered into the wellbore 22 by a means of an armored electrical cable 30. The cable 30 can be spooled and unspooled from a winch or drum 48. The tool string 32 can be electrically connected to surface equipment 54 by an insulated electrical conductor (not shown separately in FIG. 1) forming part of the cable 30. The surface equipment 54 can include one part of a telemetry system 38 for communicating control signals and data to the tool string 32 and computer 40. The computer can also include a data recorder 52 for recording measurements made by the apparatus and transmitted to the surface equipment 54.

An NMR probe 42 according to the present invention can be included in the tool string 32. The tool string 32 is preferably centered within the wellbore 22 by means of a top centralizer 56 and a bottom centralizer 57 attached to the tool string 32 at axially spaced apart locations. The centralizers 56, 57 can be of types known in the art such as bowsprings.

Circuitry for operating the NMR probe 42 can be located within an NMR electronics cartridge 44. The circuitry can be connected to the NMR probe 42 through a connector 50. The NMR probe 42 is typically located within a protective housing 43 which is designed to exclude the drilling mud 34 from the interior of the probe 42. The function of the probe 42 will be further explained.

Other well logging sensors (not shown separately for clarity of the illustration in FIG. 1) may form part of the tool string 32. As shown in FIG. 1, one additional logging sensor 47 may be located above the NMR electronics cartridge 44. Other logging sensors, such as shown at 41 and 46 may be located within or below the bottom centralizer 57. The other sensors 41, 46, 47 can be of types familiar to those skilled in the art and can include, but are not limited to, gamma ray detectors, formation bulk density sensors or neutron porosity detectors. Alternatively, parts of the NMR electronics may be located within electronic cartridges which form part of other logging sensors. The locations of the other sensors 41, 46, 47 shown in FIG. 1 are a matter of convenience for the system designer and are not to be construed as a limitation on the invention.

Figure 2:
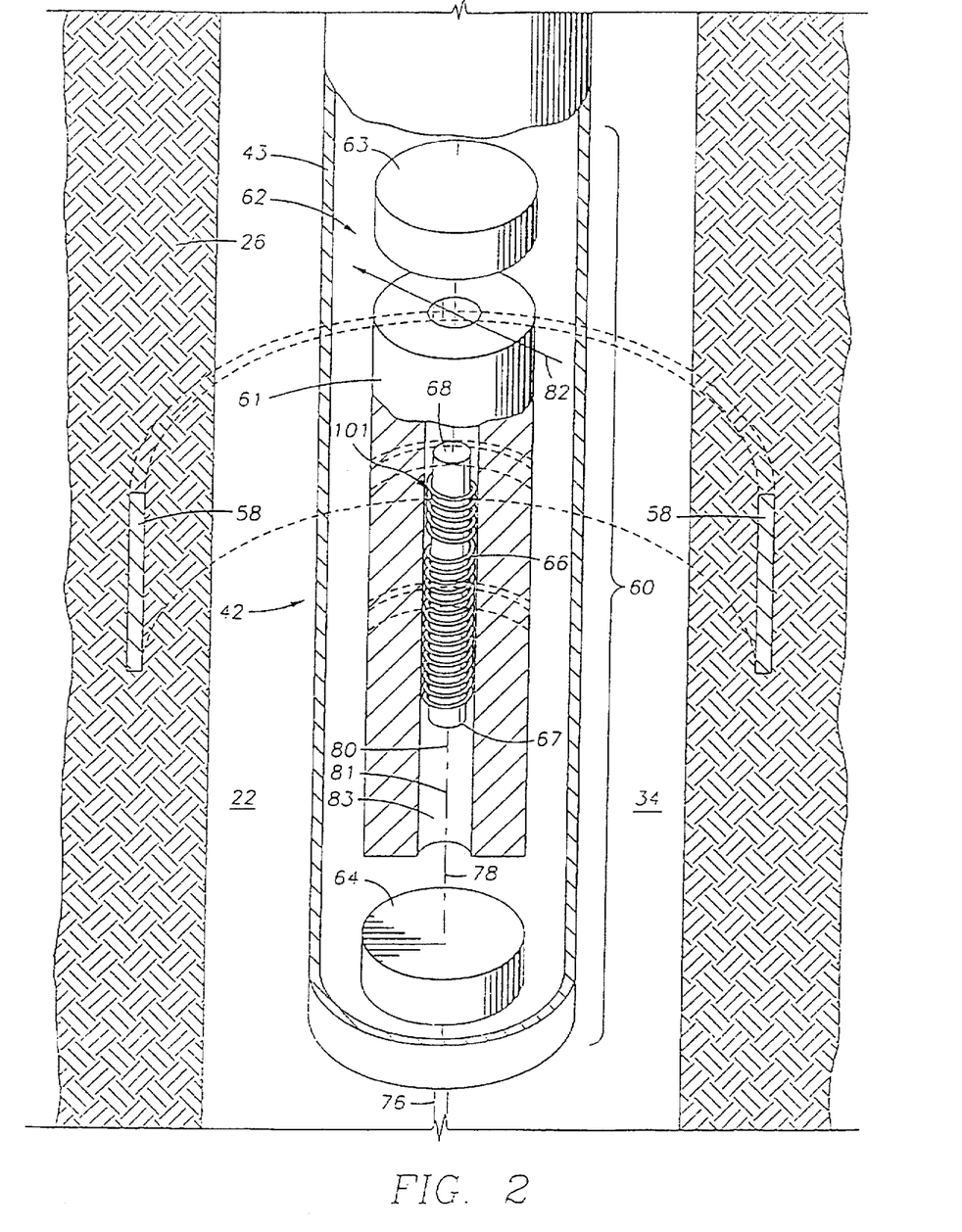
FIG. 2 shows the NMR probe of the present invention in more detail.

FIG. 2 shows the NMR probe 42 in more detail. The NMR probe 42 preferably comprises a generally cylindrical permanent or electro- magnet assembly 60. The magnet assembly 60 can include at least one permanent magnet 62, which preferably has a substantially circular cross section and is generally elongated along a magnet axis 80. The magnet axis 80 is preferably positioned coaxially with the longitudinal axis 76 of the wellbore (22 in FIG. 1). Alternatively, a plurality of permanent magnets may be used to make the magnet assembly 60. For clarity of the description of the invention, the one or more permanent magnets 62 will be considered together and referred to as permanent magnet 62, and their common axis 80 and the collocated axis of the wellbore (22 in FIG. 1) will be jointly identified herein as the longitudinal axis, shown at 78.

The permanent magnet 62 preferably has substantially uniform magnetization along the longitudinal axis 78. The magnet 62 also preferably has a magnetization direction 82 which is substantially perpendicular to the longitudinal axis 78. The permanent magnet 62 should have an overall length along the longitudinal axis 78 which is greater than twice the dimension of the permanent magnet 62 perpendicular to the longitudinal axis 78. The overall length of the permanent magnet 62 should also generally be greater than twice the diameter of the sensitive volme 58.

The permanent magnet 62 preferably comprises a main permanent magnet 6 1, a top end magnet 63 located above the main permanent magnet 61 and a bottom end magnet 64 located below the main permanent magnet 61. The end magnets 63, 64 are provided to reduce axial asymmetry of the static magnetic field generated by the permanent magnet 62 in the sensitive volume 58.

The main permanent magnet 61 is preferably formed into an annular cylinder having a hole 83 of substantially circular cross section. The axis 81 of the magnet hole 83 is preferably parallel to the longitudinal axis 78. Details of the static magnetic field imparted by the permanent magnet 62 within the sensitive volume 5 8 and within the magnet hole 83 will be further explained. It is to be understood that the cylindrical shape of the permanent magnet 62 and the hole 83 are preferred but not essential. A preferred feature of the magnet 62 is that the direction of the static magnetic field induced by the magnet 62 be substantially perpendicular to the longitudinal axis 78. If the shape of the magnet 62 is other than cylindrical, for example, elliptical, the hole 83 should have the same general shape and the same ratio of long axis to short axis as the magnet 62 in order that the static magnetic field inside the hole 83 be substantially equal to zero.

The main permanent magnet 61 can be made from a ferrite magnet material such as that sold under the trade name "Spinalor" and manufactured by Ugimag, 405 Elm St., Valparaiso, Ind., or another material sold under the trade name "Permadure" and manufactured by Philips, 230 Duffy Ave., Nicksville, N.Y. The permanent magnet material of the main permanent magnet 61 should be electrically nonconductive, so that an antenna used to generate a radio frequency magnetic field can be located in the hole 83.

The top end magnet 63 and the bottom end magnet 64 may be formed from the same or similar ferrite permanent magnet material as is the main permanent magnet 61. Alternatively, the end magnets 63, 64 may be formed form magnetically stronger material such as a neodymium-iron-boron magnet alloy sold under the trade name "Ugistab" and manufactured by Ugimag, 405 Elm St., Valparaiso, Ind., or another material sold under trade name "Vacodym" and manufactured by Vacuumschmelze GMBH, 9/7 Rhenaniastrasse St., Berlin, Germany. Alternatively, the top end magnet 63 and the bottom end magnet 64 may be formed from samarium-cobalt permanent magnet material such as one sold under trade name "Recoma" and manufactured by Ugimag, 405 Elm St., Valparaiso, Ind., or another sold under trade name "EEC" and manufactured by Electron Energy Corp., 924 Links Ave., Landsville, Pa. The material forming the top end magnet 63 and the bottom end magnet 64 need not be electrically non-conductive.

The magnet 62 described in the present embodiment of the invention generates a static magnetic field which generally decreases in amplitude as the radial distance from the longitudinal axis 78 increases. It is to be understood that this characteristic of the magnet 62 is a convenience for the system designer and is not to be construed as a limitation on the structure of magnet which will perform as required in the present invention. The characteristics of the magnet 62 necessary to the present invention will be further explained.

The NMR probe 42 further includes the previously described transceiver antenna 67, which can comprise one or more coil windings 66 preferably arranged inside the hole 83 in the main permanent magnet 61. The coil windings 66 are preferably arranged so that each coil winding 66 lies substantially in a plane perpendicular to the longitudinal axis 78. Radio frequency (RF) alternating current passing through the coil windings 66 generates an RF magnetic field in the earth formation 26 in FIG. 1). The RF magnetic field generated by the current flow in the coil windings 66 has field directions substantially parallel to the longitudinal axis 78 within the sensitive volume 58.

The coil windings 66 should have an overall length parallel to the longitudinal axis 78 which is about equal to the diameter of the sensitive volume 58. The overall length of the coil windings 66 parallel to the longitudinal axis 78 preferably should be substantially shorter than the overall length of the main permanent magnet 62 along the longitudinal axis 78.

Preferably, the coil windings 66 are formed around a soft ferrite rod 68. The soft ferrite rod 68 can be formed from material such as that sold under trade designation "F6" and manufactured by MMG-North America, 126 Pennsylvania Ave., Paterson, N.J., or another sold under trade designation "3C2" and manufactured by Philips, 230 Duffy Ave., Nicksville, N.Y. The ferrite rod 68 preferably is located coaxially with the longitudinal axis 78. The overall length of the ferrite rod 68 along the longitudinal axis 78 should be substantially less than the length of the permanent magnet 62 along the longitudinal axis 78. Alternatively, a plurality of coils and a plurality of ferrite rods may be employed. The assembly of coil windings 66 and soft ferrite rod 68 will be referred to hereinafter as the transceiver antenna 67. The ferrite rod 68 has the particular function of increasing the field strength of the RF magnetic field generated by the transceiver antenna 67. Using the ferrite rod 68 particularly enables the transceiver antenna 67 to have a relatively small external diameter so that it can be located in the hole 83. Having a small external diameter particularly enables the transceiver antenna 67 of the present invention to be sized so that the apparatus of the present invention can be used in smaller diameter wellbores.

The transceiver antenna 67 also can include a frequency control coil 101, which can be another wire coil wound around the ferrite rod 68. As will be further explained, a control voltage selectable by the system operator can be applied to the frequency control coil 101 to tune the transceiver antenna 67 when the frequency of the RF source 93 is changed.

The frequency of the RF magnetic field will determine the amplitude of the static magnetic field 62 in which a nuclear magnetic resonance condition is induced. The amplitude of the static magnetic field will affect the magnitude of internal magnetic field gradients developed within the pore spaces of a porous medium when there is a difference between the magnetic susceptibility of fluid in the pore spaces of the medium and the matrix of the medium. Changing the frequency of the RF magnetic field will change the static magnetic field amplitude in which the resonance condition is induced. Since the magnet 62 as previously described provides a static magnetic field which has a distribution of different amplitudes, by changing the frequency of the RF magnetic field, the resonant condition can be induced within a plurality of different static magnetic field amplitudes and corresponding different internal magnetic field gradients. The significance of this feature of the present embodiment will be further explained.

Figure 3:
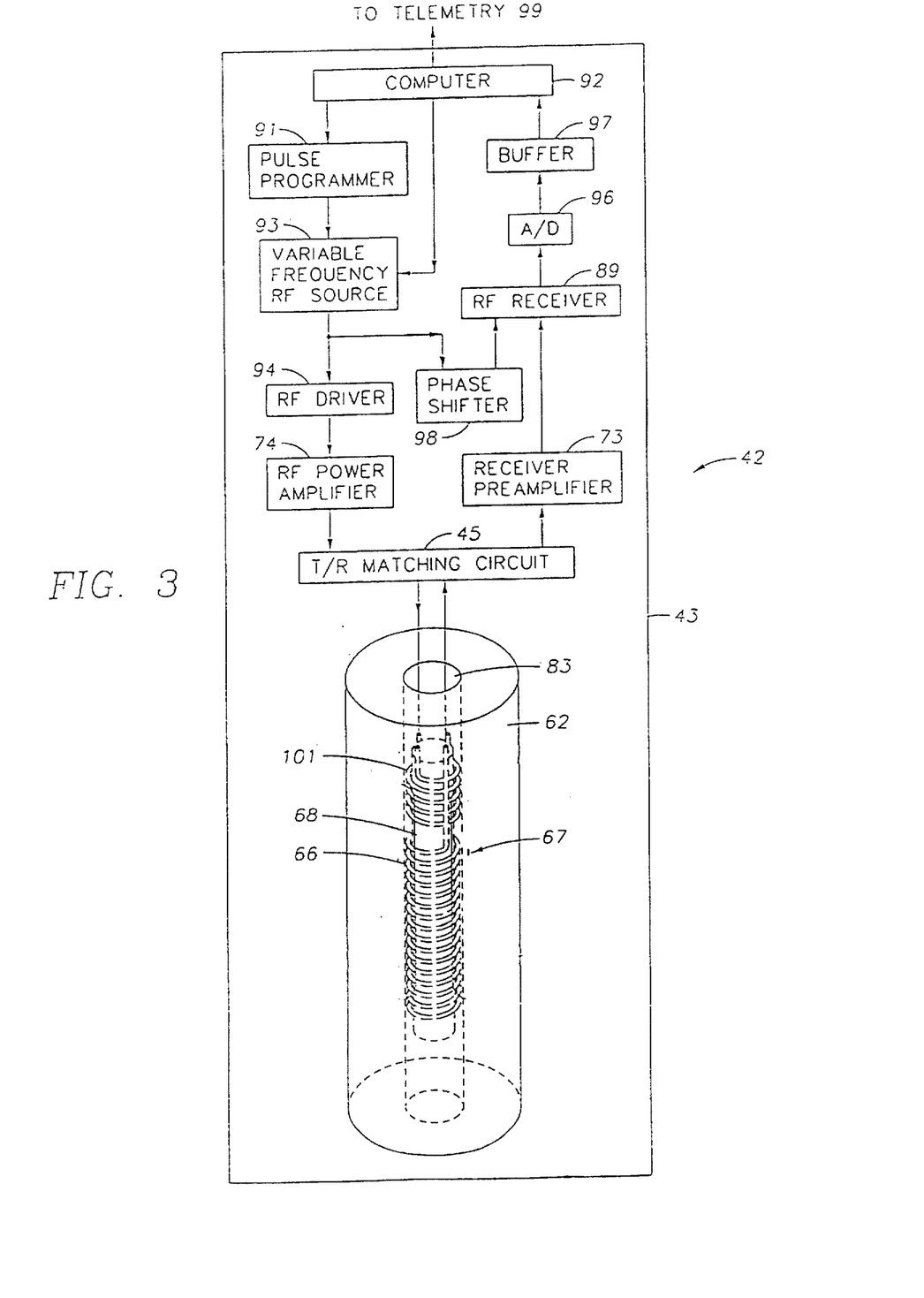
FIG. 3 shows a functional block diagram of the NMR probe of the present invention.

FIG. 3 shows, in general form, the NMR probe 42 and a functional block diagram of the NMR well logging apparatus according to the present invention. A transmitter/receiver (T/R) matching circuit 45 can be disposed within the housing 43. The T/R matching circuit 45 typically includes a series of resonance capacitors (not shown separately), a transmitter/receiver switch (not shown separately) and both "to-transmitter" and "to-receiver" matching circuitry. The T/R matching circuit 45 can be coupled both to a radio frequency (RF) power amplifier 74 and to a receiver preamplifier 73. While shown as located inside the housing 43 the T/R matching circuit 45, the RF power amplifier 74 and the receiver preamplifier 73 may alternatively be located outside the housing 43 within the top centralizer (56 in FIG. 1) or within the NMR electronics cartridge (44 in FIG. 1). The locations of the T/R matching circuit 45, the RF power amplifier 74 and the receiver preamplifier 73 are not to be construed as a limitation on the invention.

Part of the control circuitry for the NMR logging apparatus includes a down-hole computer 92, which among other functions provides control signals to a pulse programmer 91. The computer 92 and the pulse programmer 91 may also be located within the top centralizer 56 or in the NMR electronics cartridge 44. The pulse programmer 91 receives an RF signal input from a variable frequency RF signal source 93. The pulse programmer 91 controls the timing and operation of both the variable frequency RF signal source 93 and an RF driver 94. The RF driver 94 receives an input from the variable frequency RF source 93 and provides an output to the RF power amplifier 74. The RF power amplifier 74 provides a high power signal to drive the transceiver antenna 67 for generating an RF magnetic field in the sensitive volume (58 in FIG. 1). The RF power amplifier 74 can be electrically connected (typically by the switch in the T/R matching circuit 45) to the transceiver antenna 67 during transmission of RF power pulses.

During reception of the induced NMR signal, the transceiver antenna 67 can be electrically connected to the receiver preamplifier 73. The output of the RF receiver preamplifier 73 is provided to an RF receiver 89. The RF receiver 89 also receives a phase reference input from a phase shifter 98. The phase shifter 98 receives a primary phase reference input from the variable frequency RF source 93. The RF receiver 89 provides an output to an A/D converter 96. The A/D converter 96 output can be stored in a buffer 97 until required for use by the down-hole computer 92. Alternatively, the buffer 97 contents can be conducted directly to a downhole part of the telemetry unit 99 for transmission to the surface equipment (54 in FIG. 1).

The downhole computer 92 typically preprocesses the data from the buffer 97 and transfers the preprocessed data to the downhole portion of the telemetry system, shown generally at 99. The downhole portion of the telemetry system 99 transmits the preprocessed data to the telemetry unit (38 in FIG. 1) in the surface equipment (54 in FIG. 1). The telemetry unit 38 transfers the data to the surface computer (40 in FIG. 1) for calculating and presenting desired well logging output data for further use and analysis as is understood by those skilled in the art.

All of the elements described herein and as shown in FIG. 3, except the transceiver antenna 67 and the magnet assembly (60 in FIG. 2), at the convenience of the system designer may be disposed within the housing 43, the top centralizer (56 in FIG. 1) or the NMR electronics cartridge (44 in FIG. 1). These same elements may alternatively be located at the earth's surface, for example in the surface equipment 54 using the cable (30 in FIG. 1) for transmission of electrical power and signals to the transceiver antenna 67 and the additional receiver antenna 70.

2. Principles of Measurement

NMR spin-echo measurements and NMR apparatus for measuring properties of earth formations penetrated by wellbores are known in the art. U.S. Pat. No. 4,710,713 issued to Taicher et al, for example, describes one such apparatus. U.S. Pat. No. 5,212,447 issued to Paltiel, for example, describes methods of using NMR measurements to determine an indicator of fluid mobility within porous media referred to as the "self-diffusion constant" D. The diffusion constant can be determined from NMR spin-echo experiments according to the following expression:

$$A(n) = A\exp\left[-2n\tau\left(\frac{1}{T_2} + \frac{D\gamma^2G^2\tau^2}{3}\right)\right] \quad (3)$$

wherein A represents the NMR signal amplitude at zero time, $A(n)$ represents the amplitude of the n-th spin echo signal, $\gamma$ represents the gyromagnetic ratio of the nuclei subject to the NMR excitation (usually hydrogen), $\tau$ represents the time interval between successive radio frequency (RF) spin-reorientation pulses and G represents the gradient of the static magnetic field. $T_2$ represents the intrinsic transverse relaxation time and can be measured directly if the gradient G is equal to zero, or if $\tau$ is very small.

As is understood by those skilled in the art, differences in magnetic susceptibility between the solid matrix, and fluid in the pore space of porous media (which include earth formations) can result in random internal magnetic field gradients being established when a magnetic field is applied to such media. The internal gradients $G_i$ are typically proportional to the magnitude of the applied magnetic field $H_0$ as described in, J. A. Glasel and K. H. Lee, *On the Interpretation of Water Nuclear Magnetic Resonance Relaxation Times in Heterogeneous Systems*, Journal of the American Chemical Society, vol. 96, p 970 (1974). For a particular simplified model:

$$G_i = \left[\frac{\Delta\chi}{4R_p}\right]H_0 = \alpha H_0 \quad (4)$$

where a constant of proportionality, related to the difference in magnetic susceptibility between the matrix and fluid with respect to the average radius of the pore spaces, is represented by $\alpha$. As a result of these internal magnetic field gradients, equation (3), the basic relationship of spin-echo amplitude, can be approximated according to the following expression:

$$A(n) = A\exp\left[-2n\tau\left(\frac{1}{T_2} + \frac{D\gamma^2\tau^2}{3} <(G_0+G_i)^2>\right)\right] \quad (5)$$

where $G_0$ represents the gradient of the static magnetic field. The average value of the internal gradients, however, is substantially equal to zero, so that:

$$<(G_0+G_i)^2> = G_0^2 + <G_i^2> \quad (6)$$

and by substitution of equation (4), the expression for the spin-echo amplitudes can be approximated by the following expression:

$$A(n) = A\exp\left[-2n\tau\left(\frac{1}{T_2} + \frac{D\gamma^2\tau^2}{3}(G_0^2 + \alpha^2H_0^2)\right)\right] \quad (7)$$

$\tau$ can be selectable by the system designer and/or the system operator. By selecting a value of $\tau$ which is small enough to make the diffusion related term of equation (7) negligible in value, the spin-echo amplitudes can be used to determine A and $T_2$. Assuming the static magnetic field gradient is negligibly small or is known and the parameter $\alpha$ is either known or can be determined (see for example, P. Nelson, *Magnetic Susceptibility Logs From Sedimentary and Volcanic Environments* Transactions of the 34th Annual Logging Symposium, Jun. 13–16, 1993, Society of Professional Well Log Analysts, Houston, Tex.), the self-diffusion constant can be determined by measuring NMR spin-echo amplitudes in a single spin-echo experiment. By contrast, methods disclosed in the prior art required application of a static magnetic field having a substantial gradient.

It can also be determined from equation (7) that using NMR measurements made within a static magnetic field having only a single magnitude of gradient (related to the parameter α and assumptions made in deriving α) is insufficient to determine the self-diffusion constant when the internal magnetic field gradient is not known.

By determining A and $T_2$, the self-diffusion constant can be readily determined by measuring NMR spin-echo amplitudes made at two different values of total magnetic field gradient. Prior art methods of changing the gradient include the pulsed gradient technique, described in, L. L. Latour et al, *Time-Dependent Diffusion Coefficient of Fluids on Porous Media as a Probe of Surface-to-Volume Ratio*, Journal of Magnetic Resonance, vol. 101, pp 342–346 (1993). An apparatus such as the one disclosed in the Paltiel '447 patent cited herein may be useful in performing a method similar to the one described in the Latour reference.

The present invention, however, uses the internal gradients induced in the porous medium in response to the applied static magnetic field in order to determine the diffusion constant. Generally, the present invention can be described as determining the motion properties of fluid in a porous medium using internal magnetic field gradients generated within the porous medium without the necessity of imposing a variable external gradient magnetic field on the porous medium. The internal magnetic field gradients caused by difference in magnetic susceptibilities between the medium and the fluid in the pore spaces are typically sufficient to enable determination of the self-diffusion constant.

By the principle that the internal magnetic field gradients are related in magnitude to the amplitude of the applied static magnetic field and to the difference in magnetic susceptibility, it has been determined that it is not necessary to change the applied static magnetic field gradient in order to make the two measurements needed to determined the diffusion constant. In the present embodiment of the invention it is only necessary to change the amplitude of the applied static magnetic field.

As previously explained herein, the magnet (62 in FIG. 2) of the present embodiment of the invention provides a convenient structure for inducing a static magnetic field having varying amplitude, but this structure is not to be construed as a limitation on the invention. It is contemplated that a magnet structure which provides a static magnetic field having a region of substantially zero gradient for at least two different values of amplitude could also be used in the present invention. It is also to be understood that while changing the gradient of the static magnetic field is not necessary to perform the method of the present invention, if the static magnetic field gradient does change correspondingly to the static magnetic field amplitude it will not impair the function of the present invention as long as the static field gradient and the static field amplitude do not change in direct proportion.

The present embodiment of the invention can readily make NMR spin-echo measurements within two different amplitudes of the static magnetic field by changing the frequency of the RF magnetic field. As previously explained, the turning of the transceiver antenna (67 in FIG. 2) can be easily changed to match the selected RF magnetic field frequency by applying a selected DC voltage to the frequency control coil (101 in FIG. 2).

Referring back to equation (4), when NMR spin-echo measurements are made at two different values of static field amplitude $H_{O1}$ and $H_{O2}$ within the porous medium, the rates at which the spin echo amplitudes decay, $R_1$ and $R_2$, respectively, can be described by the following expressions:

$$R_1 = \frac{1}{T_2} + \left[ \frac{D\gamma^2\tau^2(G_{01}^2 + \alpha^2 H_{01}^2)}{3} \right] \quad (8)$$

$$R_2 = \frac{1}{T_2} + \left[ \frac{D\gamma^2\tau^2(G_{02}^2 + \alpha^2 H_{02}^2)}{3} \right] \quad (9)$$

Using the magnet 62 structure disclosed herein will provide a static magnetic field which also has two different corresponding values of static magnetic field gradient $G_{O1}$ and $G_{O2}$. It is to be explicitly understood, however, that this feature of the static magnetic field is not required to practice the present invention. Other magnets having different static magnetic field amplitude and gradient distributions will also provide useful amplitude distributions to practice the present invention. One such magnet is described, for example, in U.S. Pat. No. 5,055,787 issued to Kleinberg et al.

The expressions in equations (8) and (9) are linear with respect to D and the product $\alpha^2 D$ and can be readily solved for D and α. It should be noted that if both external gradient values $G_{O1}$ and $G_{O2}$ are equal to zero, then D cannot be determined separately, but only as part of the product $\alpha^2 D$. As a matter of convenience for the system designer, the static magnetic field induced by the magnet 62 should include some non-zero value of gradient within a static magnetic field amplitude in which the resonance condition is to be established. In this way both α and D can be determined from the two sets of measurements. It is to be understood, however, that if α can be separately determined, as previously described, then D could be determined even without a static magnetic field gradient.

As previously explained, the present embodiment of the invention provides for selectively varying the frequency of the RF magnetic field. The RF magnetic field frequency will determine the static magnetic field amplitude in which the resonance condition is established. The magnet 62 induces a static magnetic field having an amplitude which is related to the radial distance from the axis (78 in FIG. 2) as:

$$H_O = a/r^2 \quad (10)$$

where a represents α constant of proportionality. The static magnetic field gradient $G_O$ of the magnet 62 can be represented by the expression:

$$G_O = 2H_O/r \quad (11)$$

The static magnetic field amplitude at which the resonant condition is generated depends on the RF magnetic field frequency as shown in the following expression:

$$\omega = \gamma H_O, \quad H_O = \omega/\gamma \quad (12)$$

and the static magnetic field gradient corresponding to this amplitude can be expressed as:

$$G_O = \frac{2}{a^{1/2}} \left( \frac{\omega}{\gamma} \right)^{3/2} \quad (13)$$

By substituting equations (12) and (13) for $H_O$ and $G_O$, and solving for D, the following expression for the self-diffusion constant can be obtained:

$$D = \frac{3\alpha\gamma[\omega_2^2(R_2 - 1/T_2) - \omega_1^2(R_1 - 1/T_2)]}{(2\tau\omega_1\omega_2)^2(\omega_1 - \omega_2)} \quad (14)$$

The relative error of the self-diffusion constant measurement can be determined by the expression:

$$\frac{\sigma_D}{D} = \frac{\sqrt{2} \, \sigma_R}{R_2 - R_1} \tag{15}$$

where $\sigma_D$ and $\sigma_R$, respectively, represent the standard deviations of the self-diffusion constant and the relaxation rate. The incremental relaxation rate ($R_2-R_1$) is related to the difference in frequency between the NMR measurements. The relative error in the self-diffusion constant measurements as related to the difference in the frequency of the NMR relaxation measurements can then be expressed as:

$$\frac{\sigma_D}{D} = \left[ \frac{1}{\sqrt{2} \, R} \left( \frac{\partial R}{\partial \omega} \right)_{\omega = \omega_1} (\omega_2 - \omega_1) \right]^{-1} \frac{\sigma_R}{R} \tag{16}$$

It is preferable that the difference in frequency be as large as is practical to improve the accuracy of the measurement of the self-diffusion constant.

DESCRIPTION OF AN ALTERNATIVE EMBODIMENT

The principle of operation the present invention is related to the fact that internal magnetic field gradients are generated in the pore spaces of a porous medium when there is a difference in magnetic susceptibility between the matrix of the medium (the solid portion of a porous earth formation, for example) and the fluid present in the pore spaces of the medium. In the first embodiment, it was shown that a solution for the self-diffusion constant may be obtained without application of more than one static magnetic field gradient. It is only necessary, in the first embodiment, to apply different values of amplitude of the static magnetic field to the medium.

The present embodiment enables determination of the self-diffusion constant by selectively filling the pore spaces of the medium with a fluid having a known difference in magnetic susceptibility from the porous medium. Nuclear magnetic resonance measurements can be made at a single frequency using the apparatus disclosed herein. The static magnetic field will then generate substantially known values of internal magnetic field gradients within the pore spaces since the difference in susceptibility between the matrix and the fluid is substantially known. The self-diffusion constant can then be calculated from NMR spin echo amplitude measurements using an expression similar to the one in equation (7) as described in the first embodiment.

One way of introducing such a fluid into the pore spaces of the porous medium is for the drilling mud (34 in FIG. 1) to include a liquid phase having a known magnetic susceptibility. As is understood by those skilled in the art, the liquid phase of the drilling mud 34 intrudes into ("invades") the pore spaces of the earth formations (such as 22 in FIG. 1) as a result of differential pressure. The frequency of the RF magnetic field can be selected to excite nuclei near the wellbore wall so that the excited nuclei will substantially include those of the liquid phase of the drilling mud 34. Other methods of introducing a particular fluid into the pore spaces are well known and can be used to practice the present invention. Using drilling mud having known magnetic susceptibility should not be construed as a limitation on this embodiment of the invention.

It is also possible to perform self-diffusion measurements on fluid suspensions using the present invention. For example, water and oil have different magnetic susceptibilities. A suspension of water and oil will typically respond to application of a static magnetic field in similar manner as a fluid-filled porous medium where there is a difference in magnetic susceptibility between the porous matrix and the fluid. Internal magnetic field gradients will be induced in one phase of the suspension just as in the pores of the porous medium. The self-diffusion constant can be determined just as for the fluid in the porous medium.

As previously described, solution of equations (8) and (9) enables estimation of the internal gradient parameter $\alpha$ in addition to the self-diffusion constant. This parameter may be of particular interest in the study of porous media such as earth formations penetrated by a wellbore.

Those skilled in the art will readily devise other embodiments of the present invention which do not depart from the spirit of the invention disclosed herein. Accordingly, the invention should be limited in scope only by the attached claims.

What is claimed is:

1. A method of determining self-diffusion properties of nuclei within pore spaces of a porous medium, comprising the steps of:

applying a first static magnetic field to said porous medium to polarize said nuclei, said magnetic field generating internal magnetic field gradients within said pore spaces, wherein a difference in magnetic susceptibility between a fluid in said pore spaces and a solid matrix of said medium is known;

applying a radio frequency magnetic field to said medium at a first frequency to excite said nuclei;

receiving nuclear magnetic resonance signals from said nuclei at said first frequency;

calculating said self-diffusion properties from amplitudes of said nuclear magnetic resonance signals.

2. The method as defined in claim 1 further comprising substantially filling said pore spaces with a fluid so as to cause a known internal magnetic field gradient within said pore spaces.

3. The method as defined in claim 2 wherein said step of substantially filling said pore spaces comprises drilling a wellbore through earth formations with drilling mud having a liquid phase of known magnetic susceptibility.

4. A method for determining self-diffusion properties of a fluid within pore spaces of an earth formation comprising the steps of:

applying a first static magnetic field having a first amplitude to said earth formation, said first static magnetic field inducing gradients within said pore spaces, wherein a difference in magnetic susceptibility between a fluid in said pore spaces and a solid matrix of said medium is known;

generating a radio frequency magnetic field to excite said nuclei within said pore spaces, said radio frequency magnetic field having a first frequency corresponding to said first amplitude;

receiving nuclear magnetic resonance signals from said excited nuclei; and calculating said self-diffusion properties from amplitudes of said nuclear magnetic resonance signals.

5. The method as defined in claim 4 further comprising substantially filling said pore spaces with a fluid so as to result in a known internal magnetic field gradient being induced within said pore spaces as a result of application of said first static magnetic field.

6. The method as defined in claim 5 wherein said step of substantially filling said pore spaces comprises drilling a wellbore through said earth formations with drilling mud having a liquid phase of known magnetic susceptibility.

7. The method as defined in claim 4 further comprising:

applying a magnetic field gradient to said earth formation;

repeating said step of generating said radio frequency magnetic field; and repeating said step of receiving said nuclear magnetic resonance signals, wherein said step of calculating said self-diffusion properties comprises determining rates of decay of said amplitudes of said nuclear magnetic resonance signals received with said gradient applied and received without said gradient applied.

8. The method as defined in claim 7 wherein said step of applying said magnetic field gradient comprises applying a second static magnetic field having a second amplitude different than said first amplitude, said second static magnetic field including said gradient therewith, and wherein repeating said step of applying said radio frequency magnetic field is performed at a second frequency corresponding to said second amplitude.

9. A method of measuring self-diffusion properties of nuclei within pore spaces of a porous medium, comprising the steps of:

applying a static magnetic field to said medium to polarize said nuclei, said static magnetic field having a first amplitude, a second amplitude and a gradient;

applying a radio frequency magnetic field at a first frequency to excite said nuclei, said first frequency corresponding to said first amplitude;

receiving nuclear magnetic resonance signals from said excited nuclei at said first frequency;

applying said radio frequency magnetic field at a second frequency to excite said nuclei, said second frequency corresponding to said second amplitude, said static magnetic field at said second amplitude including said gradient therewith;

receiving said nuclear magnetic resonance signals from said excited nuclei at said second frequency;

calculating said self-diffusion properties from amplitudes of said nuclear magnetic resonance signals received at said first and said second frequencies.

10. The method as defined in claim 9 wherein said step of calculating said self-diffusion properties comprises determining rates of decay of said amplitudes of said nuclear magnetic resonance signals received at said first and said second frequencies.

11. The method as defined in claim 9 wherein said step of calculating said self-diffusion properties includes determining a difference in magnetic susceptibility between said porous medium and a fluid disposed within said pore spaces of said medium.

12. A method of determining self-diffusion properties of nuclei within pore spaces of a porous medium, comprising the steps of:

applying a first static magnetic field to said porous medium to polarize said nuclei, said magnetic field generating internal magnetic field gradients within said pore spaces;

substantially filling said pore spaces with a fluid so as to cause a known internal magnetic field gradient within said pore spaces;

applying a radio frequency magnetic field to said medium at a first frequency to excite said nuclei;

receiving nuclear magnetic resonance signals from said nuclei at said first frequency;

calculating said self-diffusion properties from amplitudes of said nuclear magnetic resonance signals.

13. The method as defined in claim 12 wherein said step of substantially filling said pore spaces comprises drilling a wellbore through earth formations with drilling mud having a liquid phase of known magnetic susceptibility.

14. A method of determining self-diffusion properties of nuclei within pore spaces of a porous medium, comprising the steps of:

applying a first static magnetic field to said porous medium to polarize said nuclei, said magnetic field generating internal magnetic field gradients within said pore spaces;

applying a radio frequency magnetic field to said medium at a first frequency to excite said nuclei;

receiving nuclear magnetic resonance signals from said nuclei at said first frequency;

applying to said medium a second static magnetic field having an amplitude different from an amplitude of said first static magnetic field, said second static magnetic field including a non-zero magnitude gradient;

applying said radio frequency magnetic field at a second frequency so as to excite said nuclei;

receiving said nuclear magnetic resonance signals at said second frequency; and calculating said self-diffusion properties by determining rates of decay of said amplitudes of said nuclear magnetic resonance signals received at said first and at said second frequencies.

15. A method of measuring self-diffusion properties of nuclei within pore spaces of a porous medium, comprising the steps of:

applying a static magnetic field to said medium to polarize said nuclei, said static magnetic field having a first amplitude, a second amplitude and a gradient;

applying a radio frequency magnetic field at a first frequency to excite said nuclei, said first frequency corresponding to said first amplitude;

receiving nuclear magnetic resonance signals from said excited nuclei at said first frequency;

applying said radio frequency magnetic field at a second frequency to excite said nuclei, said second frequency corresponding to said second amplitude, said static magnetic field at said second amplitude including said gradient therewith;

receiving said nuclear magnetic resonance signals from said excited nuclei at said second frequency;

calculating said self-diffusion properties from amplitudes of said nuclear magnetic resonance signals received at said first and said second frequencies by determining a difference in magnetic susceptibility between said porous medium and a fluid disposed within said pore spaces of said medium.

16. The method as defined in claim 15 wherein said step of calculating said self-diffusion properties comprises determining rates of decay of said amplitudes of said nuclear magnetic resonance signals received at said first and said second frequencies.

* * * * *